United States Patent [19]
Lawandy

[11] Patent Number: 5,851,225
[45] Date of Patent: *Dec. 22, 1998

[54] PHOTOEMITTING CATHETERS AND OTHER STRUCTURES SUITABLE FOR USE IN PHOTO-DYNAMIC THERAPY AND OTHER APPLICATIONS

[75] Inventor: Nabil M Lawandy, Providence, R.I.

[73] Assignee: Spectra Science Corporation, Providence, R.I.

[ * ] Notice: This patent issued on a continued prosecution application filed under 37 CFR 1.53(d), and is subject to the twenty year patent term provisions of 35 U.S.C. 154(a)(2).

[21] Appl. No.: 748,380

[22] Filed: Nov. 13, 1996

Related U.S. Application Data

[60] Continuation-in-part of Ser. No. 401,356, Mar. 9, 1995, Pat. No. 5,625,456, which is a division of Ser. No. 210,710, Mar. 18, 1994, Pat. No. 5,448,582.

[51] Int. Cl.$^6$ ........................................... A61N 5/01
[52] U.S. Cl. .................... 607/88; 606/7; 606/15
[58] Field of Search ................ 372/39–42, 22; 607/88, 89, 92, 93, 94; 606/3, 7

[56] References Cited

U.S. PATENT DOCUMENTS

| | | |
|---|---|---|
| 4,852,567 | 8/1989 | Sinofsky . |
| 4,957,481 | 9/1990 | Gatenby ..................................... 604/20 |
| 5,434,878 | 7/1995 | Lawandy . |
| 5,448,582 | 9/1995 | Lawandy . |
| 5,625,456 | 4/1997 | Lawandy ................................. 356/376 |

OTHER PUBLICATIONS

"Selective Absorption of UV Laser Energy by Human Atherosclerotic Plaque Treated with Tetracycline", D. Murphy–Chutorian, et al., American Journal of Cardiology, vol. 55, p. 1293, May 1985.

"Selective Absorption of Ultraviolet Laser Energy by Human Atherosclerotic Plaque Treated with Tetracycline", Douglas Murphy–Chutorian et al., American Journal of Cardiology, May 1, 1985, vol. 55, pp. 1293–1297.

*Primary Examiner*—John P. Lacyk
*Assistant Examiner*—Roy D. Gibson
*Attorney, Agent, or Firm*—Perman & Green, LLP

[57] ABSTRACT

A structure generates electromagnetic radiation having at least one wavelength selected for activating a photo-sensitive substance that is applied to a tissue to be treated. The structure is particularly useful for photo-dynamic therapy (PDT) applications. The structure includes a body of material, such as a polymer filament, band, or substrate, that contains a gain medium. The gain medium in turn contains a substance (such as dye molecules) for generating a stimulated emission that includes the at least one wavelength when excited by a pump wavelength, and a plurality of scattering sites (such as scattering particles) for scattering the stimulated emission to provide a narrow band emission at the at least one selected wavelength. The narrow band emission in turn activates the photo-sensitive therapeutic substance.

11 Claims, 3 Drawing Sheets

PHOTOEMITTING CATHETERS AND OTHER STRUCTURES SUITABLE FOR USE IN PHOTO-DYNAMIC THERAPY AND OTHER APPLICATIONS

CROSS-REFERENCE TO A RELATED PATENT APPLICATION

This patent application is a continuation-in-part of U.S. Pat. application Ser. No.: 08/401,356, filed Mar. 9, 1995, now U.S. Pat. No.: 5,625,456, issued Apr. 29, 1997, which is a divisional patent application of U.S. Pat. application Ser. No.: 08/210,710, filed Mar. 18, 1994, entitled "Optical Sources Having a Strongly Scattering Gain Medium Providing Laser-Like Action", by Nabil M. Lawandy, now U.S. Pat. No. : 5,448,582, issued Sep. 5, 1995.

FIELD OF THE INVENTION

This invention relates generally to methods and apparatus for delivering optical energy to a localized region and, in particular, to devices and methods for irradiating tissue with light having a selected wavelength or wavelengths.

BACKGROUND OF THE INVENTION

In U.S. Pat. No. 5,448,582, issued Sep. 5, 1995, entitled "Optical Sources Having a Strongly Scattering Gain Medium Providing Laser-Like Action", the inventor disclosed a multi-phase gain medium including an emission phase (such as dye molecules) and a scattering phase (such as $TiO_2$). A third, matrix phase may also be provided in some embodiments. Suitable materials for the matrix phase include solvents, glasses and polymers. The gain medium is shown to provide a laser-like spectral linewidth collapse above a certain pump pulse energy. FIGS. 13a through 13f illustrate various embodiments of the invention wherein the gain medium is contained within or on a portion of an optical fiber or catheter for providing a desired wavelength at a localized region. Reference can also be had to FIGS. 10a and 10b, wherein a structure containing the gain medium is used to provide one or more wavelengths. The structure can be used to remove, by example, undesired skin pigments by providing electromagnetic radiation at a wavelength or wavelengths that are strongly absorbed by the pigment or pigments.

Photo-dynamic therapy (PDT) is a relatively new approach to treating many cancers. Patients are injected with one or that bind to the rapidly dividing cells. A narrow-band laser is then used to excite the drugs, inducing a reaction which kills the cells. PDT has been used to treat esophageal cancer, Kaposi's sarcoma, an AIDS related condition, and the overgrowth of blood vessels in the eye (macular degeneration), which afflicts seven million people in North America alone.

One problem with current PDT techniques is that they require the use of expensive lasers to provide the various wavelengths required by current (and future) photo-sensitive drugs. The dye laser, because of its tunability, is often used for PDT applications. However, a typical dye laser can easily cost some tens of thousands of dollars. Also, the dye laser requires a complex assembly of tubing and pumps to inject a dye solution between precisely aligned mirrors. As such, the dye laser is not readily portable, and requires a significant amount of routine maintenance to remain in an operational condition. Furthermore, the dye laser requires a second laser to pump the dye solution.

As such, current PDT techniques require at least two lasers. For example, and referring to FIG. 1, a PDT excitation system 1 includes a Nd:YAG laser 2 that is used as a pump source ($\lambda_1$) for a dye laser 3, from which the desired wavelength ($\lambda_2$) of light is conducted, via a catheter 4 that contains an optical fiber, to the diseased tissue. The light is scattered on the tissue by a specially prepared tip that may include a scattering region 6 coupled to a mirror 5.

OBJECTS OF THE INVENTION

It is a first object of this invention to provide an improved method and apparatus for delivering electromagnetic radiation having a selected wavelength or wavelengths to a desired region.

It is a further object of this invention to provide a lower cost and less complex optical source for use in PDT and other therapeutic applications.

SUMMARY OF THE INVENTION

The foregoing and other problems are overcome and the objects of the invention are realized by methods and apparatus in accordance with embodiments of this invention.

In accordance with this invention a structure generates electromagnetic radiation having at least one wavelength selected for activating a photo-sensitive substance that is applied to a tissue to be treated. The structure is particularly useful for photo-dynamic therapy (PDT) applications. The structure includes a body of material, such as a polymer filament, band, or substrate, that contains a gain medium and a plurality of scattering sites, such as particles of $TiO_2$, $Al_2O$, voids, etc. The scattering gain medium generates a spectrally narrow emission (e.g., <10 nm) through, by example, the action of dye molecules and the optical feedback provided by the scattering sites when excited by a pump wavelength. The combination of the dye molecules which provide a stimulated emission and the plurality of scattering sites (such as scattering particles) that scatter the stimulated emission provide a narrow band emission at the at least one selected wavelength. The narrow band emission in turn activates the photo-sensitive therapeutic substance.

In one embodiment the body of material is further comprised of a heat-shrinkable polymer gain/scattering phase that is disposed at one end of an optical guide, such as an optical fiber.

In another embodiment the body of material is formed as a substrate that has a shape that conforms to a surface shape of the tissue to be treated.

In another embodiment the body of material is formed as one or more substrates each having a generally concave inner surface. At least one of the plurality of substrates can be nested within the other, and each provides a different wavelength selected for activating one or more photo-sensitive substances.

In embodiments of this invention the body of material is formed as a planar or non-planar substrate. Also provided is a dichroic mirror that is interposed between the substrate and a source of the pump wavelength. The dichroic mirror is transparent to the pump wavelength and reflective to the at least one wavelength selected for activating the photo-sensitive substance.

In further embodiments of this invention the body of material is comprised of a plurality of bands that are disposed circumferentially or longitudinally about a terminal end of an optical fiber. In this case different ones of the bands provide a different wavelength selected for activating one or more photo-sensitive substances.

In a still further embodiment of this invention the body of material is comprised of at least one filament that is wrapped circumferentially about a terminal end of an optical fiber.

Further in accordance with this invention there is disclosed a method for generating electromagnetic radiation having at least one wavelength selected for activating a photo-sensitive substance that is applied to a tissue to be treated. The method includes a first step of providing a substrate having a gain medium that comprises a substance for generating a stimulated emission that includes the at least one wavelength when excited by a pump wavelength, and a plurality of scattering sites for scattering the stimulated emission to provide a narrow band emission at the at least one selected wavelength. The method further includes the steps of (b) deforming the substrate so as to conform to a surface shape of the tissue to be treated; (c) applying the deformed substrate to the tissue to be treated; and (d) illuminating the deformed substrate with electromagnetic radiation having the pump wavelength to provide the narrow band emission at the at least one selected wavelength. The narrow band emission beneficially activates the photo-sensitive substance that is applied to the tissue to be treated.

Also disclosed is a method for performing photo-dynamic therapy (PDT), comprising the steps of (a) treating a tissue of interest with at least one photo-sensitive therapeutic compound that responds optimally to light having wavelengths within a predetermined band of wavelengths; (b) generating light at a location remote from the tissue; (c) transmitting the light to a structure that is positioned in close proximity to the treated tissue; (d) in response to the transmitted light, generating light in the structure, the light being generated to have a wavelength within the predetermined band of wavelengths; and (e) irradiating the treated tissue with the light having the wavelength in the predetermined band of wavelengths.

BRIEF DESCRIPTION OF THE DRAWINGS

The above set forth and other features of the invention are made more apparent in the ensuing Detailed Description of the Invention when read in conjunction with the attached Drawings, wherein.

DETAILED DESCRIPTION OF THE INVENTION

The disclosure of the above-referenced U.S. Pat. No. 5,448,582, issued Sep. 5, 1995, entitled "Optical Sources Having a Strongly Scattering Gain Medium Providing Laser-Like Action", by Nabil M. Lawandy is incorporated by reference herein in its entirety. Also incorporated by reference herein in its entirety is the disclosure of U.S. Pat. No. 5,434,878, issued Jul. 18, 1995, entitled "Optical Gain Medium Having Doped Nanocrystals of Semiconductors and also Optical Scatterers", by Nabil M. Lawandy.

Figure 1:
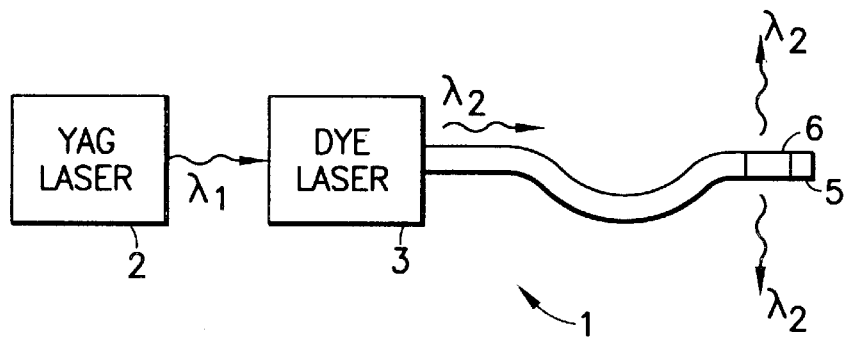
FIG. 1 illustrates a conventional laser source used in PDT.
Figure 2A:
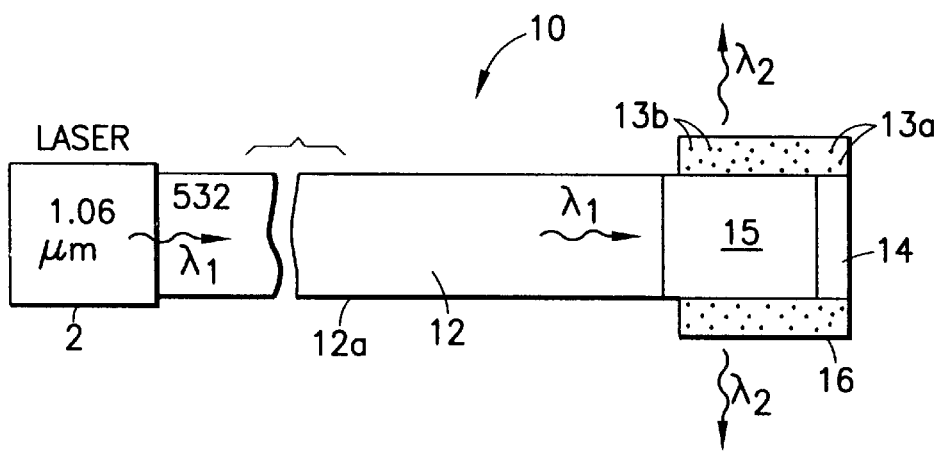
FIG. 2A is an enlarged cross-sectional view.
Figure 2B:
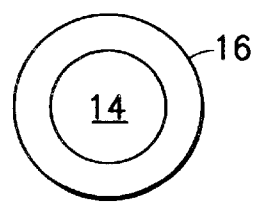
FIG. 2B is an end view, of an optical source for PDT in accordance with a first embodiment of this invention.

Reference is first made to FIGS. 2A and 2B for showing an embodiment of a catheter 10 that is suitable for use in photo-dynamic therapy applications. It should be realized, however, that the various methods and apparatus of this invention are not limited for use with only this one, albeit important, application.

The catheter 10 includes an optical fiber 12 or other suitable conduit of electromagnetic radiation, and a protective covering or sheath 12a made from, by example, a non-reactive material such as Teflon™. A first end of the catheter 10 is coupled to a laser source such as a frequency doubled or frequency tripled Nd:YAG laser 2. In the illustrated example the laser 2 provides light at a first wavelength ($\lambda_1$), such as 532 nm. The light is conveyed to a terminal end of the catheter 12 where a scattering region 15 having a mirror 14 is provided. The scattering region 15 may be comprised of silicone containing titania or other suitable scattering particles. The purpose of the region 15 is to direct the incident light out of the optical fiber 12 or light conduit and into a surrounding sheath or structure 16 that includes a gain medium as described in U.S. Pat. No. 5,488,582. That is, the sheath or structure 16 includes, by example, a selected dye molecule or molecules 13a in combination with scattering sites 13b which provide in combination a laser-like emission when stimulated by the light from the laser 2. The structure 16 outputs light with a second, desired wavelength ($\lambda_2$). In this embodiment of this invention the gain medium may be contained in a transparent polymer of a type that contracts or shrinks when heated, such as heat shrinkable tubing. The output wavelength ($\lambda_2$) is selected in accordance with the activation requirements of a photo-sensitive drug or substance used in a given PDT treatment.

Figure 3:
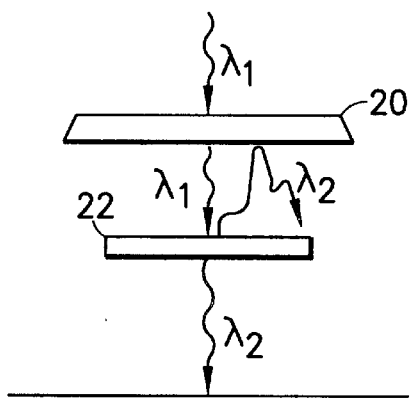
FIG. 3 is a side view of a second embodiment of a portion of an optical source for PDT.

FIG. 3 shows an embodiment wherein a dichroic mirror 20 is provided in combination with a substrate 22 that contains the gain medium. By example, the dichroic mirror 20 is transparent at the pump wavelength (e.g. 532 nm) and is reflective at the wavelength (e.g. 650 nm) that is emitted by the gain medium within the substrate 22. The substrate 22 may be a polymer, a glass, or any suitable material for containing the gain medium (e.g. dye molecules and scattering sites, such as particles of $TiO_2$ or alumina). Two known photo-sensitive drugs that are activated by 650 nm light are MPTH and Photofrin. The embodiment of FIG. 3 is well suited for treating external or exposed tissue, whereas the embodiment of FIGS. 2A and 2B is well suited for treating internal tissue.

In general, it is desirable to position the gain medium in close proximity to the tissue to be treated in order to maximize the amount of light that can be delivered to the photo-sensitive drug or drugs that are being used.

Figure 4A:
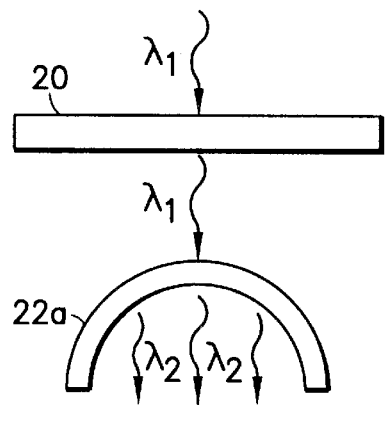
FIGS. 4A and 4B illustrate further embodiments of optical sources for PDT, in particular curved substrate embodiments.
Figure 4B:
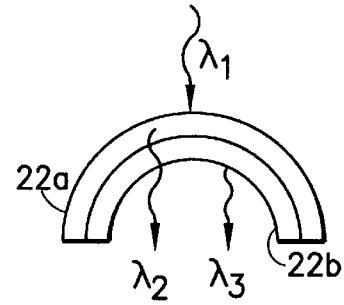

FIG. 4A shows an embodiment wherein the substrate 22 is curved, and may represent a cross-section through a hemisphere or dome. FIG. 4B illustrates an embodiment wherein a plurality of the curved substrates 22a and 22b are employed to provide at least first and second wavelengths ($\lambda_2$, $\lambda_3$). As can be seen, the substrates 22a and 22b can have a generally concave inner surface, and one may be nested or contained within the other. In both of these embodiments the substrate shape leads to an integrating sphere effect for providing a more uniform illumination of the tissue being treated. In the embodiment of FIG. 4B it is assumed that the substrate 22a is substantially transparent at $\lambda_1$, and that the substrate 22b is substantially transparent at $\lambda_2$.

Figure 5A:
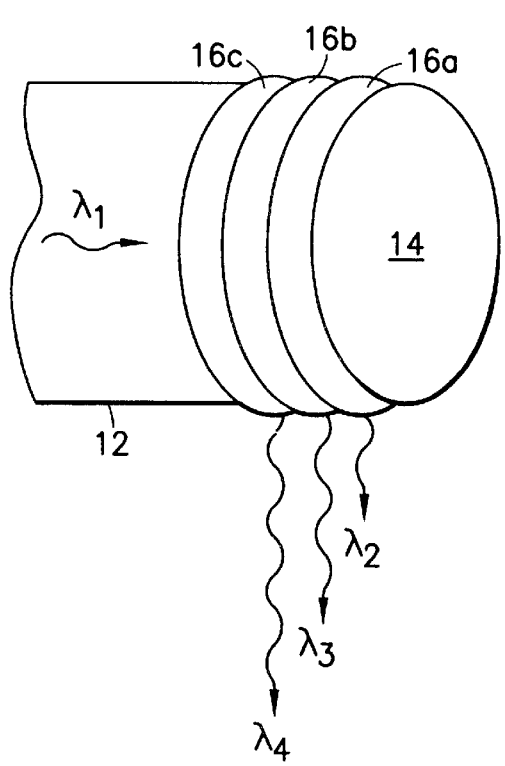
FIGS. 5A and 5B are each an enlarged view of a terminal end of a fiber optic catheter in accordance with embodiments of this invention.
Figure 5B:
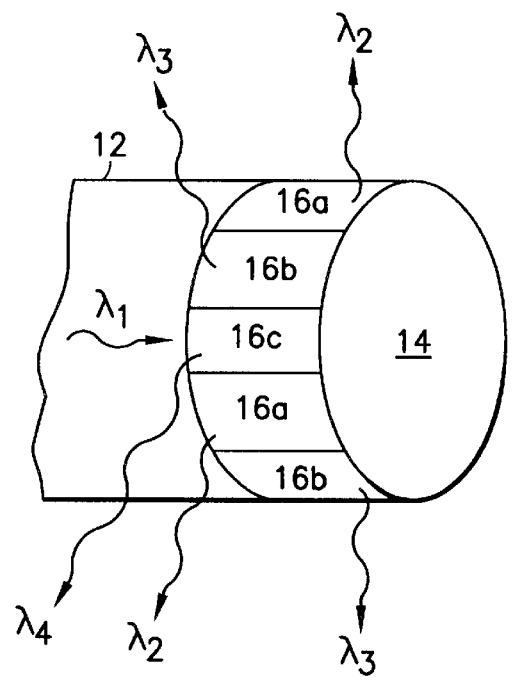

FIGS. 5A and 5B illustrate embodiments wherein a plurality of the structures 16 (e.g., sub-structures 16a–16c) are arranged circumferentially or longitudinally, respectively, about the terminal end of the optical fiber 12. Each sub-structure 16a–16c has an associated emission wavelength $\lambda_2$–$\lambda_4$, respectively. The result is the simultaneous presence of a plurality of wavelengths for simultaneously activating a plurality of photo-sensitive drugs during a PDT treatment. More or less than three sub-structures can be provided.

Figure 6:
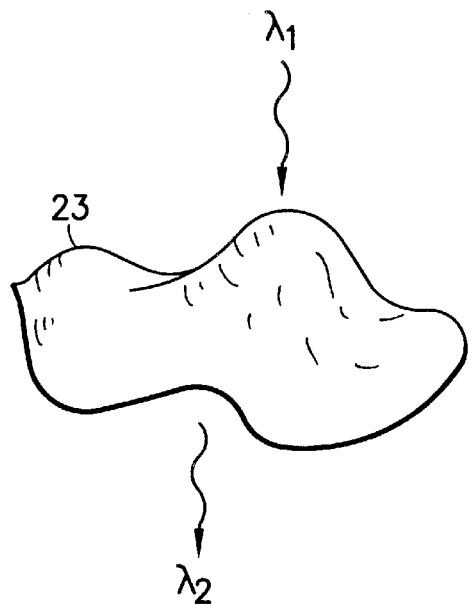
FIG. 6 is an elevational view of a gain medium containing substrate having a predetermined three dimensional shape for conforming to a region of tissue to be treated.

FIG. 6 illustrates an embodiment of the invention wherein a gain medium-containing substrate 23 is given a predetermined three-dimensional shape for conforming the substrate to a shape of a region of tissue to be treated. By example, a mold of a region of tissue to be treated (e.g, a tumor) is made, and the substrate 23, such as polymeric material containing the gain medium, is formed from the mold. Alternatively, a three dimensional surface profile or map of the region of tissue can be obtained from a medical imaging technique (e.g., CAT scan or NMR image), and the shape of the substrate 23 conformed to the profile. This embodiment of the invention is useful in providing an intimate fit between the substrate 23 and the region of tissue to be treated, thereby maximizing an amount of photo-sensitive drug or drugs that are activated.

It should be realized that the dichroic mirror 20 can also be used with the embodiment of FIG. 6, as well as the embodiment of FIG. 4B.

Figure 7:
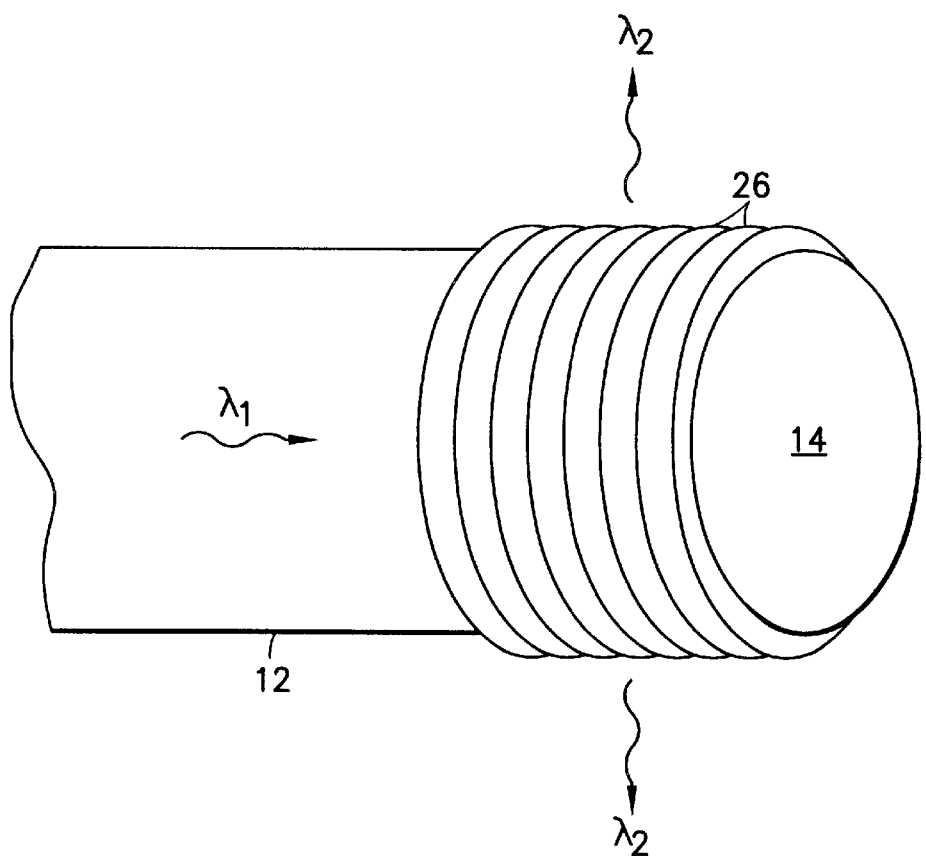
FIG. 7 is an enlarged view of a terminal end of a fiber optic catheter in accordance with a further embodiment of this invention.

FIG. 7 illustrates a further embodiment of this invention wherein the terminal end of the optical fiber 12 is wrapped with one or more polymer filaments 26 that contain the gain medium. Preferably adjacent wraps of the filaments 26 touch one another to prevent any leakage of the light at $\lambda_1$. A plurality of different filaments can be used for providing a plurality of different wavelengths of light for activating a plurality of photo-sensitive drugs.

A suitable laser system for driving this and other embodiments of this invention is a 15 mJ, 1000 Hz PRR, 532 nm laser available from Continuum. In general, a diode pumped Nd:YAG laser can be employed to provide a compact and relatively low cost source. In other embodiments a pure silica fiber 12 can be used with an ultraviolet (UV) source operating at, by example, 400 nm, and can provide an emission of, by example, 1.7 micrometers, depending on the characteristics of the selected gain medium.

It can be realized that the teaching of this invention provides the ability to readily provide a number of different wavelengths of therapeutic light, while avoiding the problems inherent in providing, operating, and maintaining a conventional tuneable light source, such as a dye laser.

In a further embodiment of this invention the dye molecules that comprise a portion of the gain medium may be replaced by semiconductor nanocrystals selected for their emission wavelength(s) (e.g., GaN for blue, ZnSe for green, CdSe for red). In this case the semiconductor nanocrystals may also function as scattering sites for the stimulated emission, either alone or in combination with the scattering particles. In a still further embodiment of this invention the polymer structure or substrate itself may provide the stimulated emission, such as a polymer comprised of PPV or MEHPPV.

Although described above in the context of specific materials, dimensions and the like, it should be appreciated that the teaching of this invention is not intended to be limited to only these disclosed exemplary embodiments and values. Neither is the teaching of this invention intended to be limited to only the specific catheter and other embodiments described above.

As such, while the invention has been particularly shown and described with respect to preferred embodiments thereof, it will be understood by those skilled in the art that changes in form and details may be made therein without departing from the scope and spirit of the invention.

What is claimed is:

1. A method for performing photo-dynamic therapy (PDT), comprising the steps of:

treating a tissue of interest with at least one photo-sensitive therapeutic compound that responds to light having wavelengths within a predetermined band of wavelengths;

providing a structure that is positioned such that light generated in the structure will irradiate the tissue of interest, the structure comprising a gain medium that comprises a substance for generating a stimulated light emission that includes a selected wavelength, the structure further comprising a plurality of scattering sites for scattering the stimulated light emission to provide a narrow band emission at the selected wavelength;

generating excitation light at a location remote from the tissue of interest;

transmitting the excitation light to the structure;

in response to the transmitted excitation light, generating light in the structure, the light being generated to have the selected wavelength within the predetermined band of wavelengths; and irradiating the tissue of interest and the therapeutic compound with the light having the selected wavelength in the predetermined band of wavelengths.

2. A method as in claim 1, wherein the step of providing provides the structure as a heat-shrinkable polymer that is disposed as at least one band about a terminal end of an optical conduit.

3. A method as in claim 1, wherein the step of providing provides the structure as a substrate that has a shape that conforms to a surface shape of the tissue of interest.

4. A method as in claim 1, wherein the step of providing provides the structure as a substrate having a generally concave inner surface.

5. A method as in claim 1, wherein the step of providing provides the structure as a plurality of substrates each having a generally concave inner surface, at least one of the plurality of substrates being nested within the other and each providing a different wavelength selected for activating one or more photo-sensitive therapeutic compounds.

6. A method as in claim 1, wherein the step of providing provides the structure as a planar or non-planar substrate, and further comprising a dichroic mirror that is interposed between the substrate and a source of the generated light, wherein the dichroic mirror is transparent to the generated light and reflective to the selected wavelength.

7. A method as in claim 1, wherein the step of providing provides the structure as a plurality of bands that are disposed circumferentially about a terminal end of an optical conduit, different ones of the bands providing a different wavelength selected for activating one or more photosensitive therapeutic compounds.

8. A method as in claim 1, wherein the step of providing provides the structure as a plurality of bands that are disposed longitudinally about a terminal end of an optical conduit, different ones of the bands providing a different wavelength selected for activating one or more photosensitive therapeutic compounds.

9. A method as in claim 1, wherein the step of providing provides the structure as at least one filament that is wrapped circumferentially about a terminal end of an optical conduit.

10. A method as in claim 1, wherein the step of providing the structure includes the steps of:

provided a substrate that is comprised of the gain medium and the plurality of scattering sites;

deforming the substrate so as to conform to a surface shape of the tissue of interest;

applying the deformed substrate to the tissue of interest; and illuminating the deformed substrate with the generated excitation light.

11. A method as in claim 1, wherein the step of providing the structure includes the steps of:

determining a surface shape of the tissue of interest;

providing a substrate that is comprised of the gain medium and the plurality of scattering sites, the substrate having a surface shape that corresponds to the determined shape;

applying the substrate to the tissue of interest; and illuminating the deformed substrate with the generated excitation light.

* * * * *